United States Patent
Sasaki et al.

(10) Patent No.: US 8,637,488 B2
(45) Date of Patent: Jan. 28, 2014

(54) **EXTRACT OBTAINED FROM *ORCHIDACEAE* PLANTS, METHOD FOR PRODUCING THE EXTRACT, AND EXTERNAL AGENT FOR SKIN COMPRISING THE EXTRACT**

(75) Inventors: Akiko Sasaki, Higashimurayama (JP); Masakazu Kawaguchi, Higashimurayama (JP); Ayaka Himono, Higashimurayama (JP)

(73) Assignee: Nichirei Biosciences, Inc., Tokyo (JP)

( * ) Notice: Subject to any disclaimer, the term of this patent is extended or adjusted under 35 U.S.C. 154(b) by 763 days.

(21) Appl. No.: 12/681,043

(22) PCT Filed: Mar. 27, 2009

(86) PCT No.: PCT/JP2009/056360
§ 371 (c)(1),
(2), (4) Date: Mar. 31, 2010

(87) PCT Pub. No.: WO2009/139231
PCT Pub. Date: Nov. 19, 2009

(65) Prior Publication Data
US 2010/0267659 A1  Oct. 21, 2010

(30) Foreign Application Priority Data

May 16, 2008 (JP) ................. 2008-129943

(51) Int. Cl.
*A61K 31/715* (2006.01)
*A61K 8/97* (2006.01)
*A61P 17/00* (2006.01)
*A61Q 19/00* (2006.01)

(52) U.S. Cl.
USPC .......................................................... 514/54

(58) Field of Classification Search
USPC ........................................................... 514/54
See application file for complete search history.

(56) References Cited

U.S. PATENT DOCUMENTS

2009/0238848 A1* 9/2009 Andre et al. ............... 424/401

FOREIGN PATENT DOCUMENTS

| JP | 59-016815 A | 1/1984 |
|---|---|---|
| JP | 2002-205933 A | 7/2002 |
| JP | 2005-179219 A | 7/2005 |
| JP | 2005-289872 A | 10/2005 |
| JP | 2007-077079 A | 3/2007 |

OTHER PUBLICATIONS

Ault, A. Techniques and Experiments for Organic Chemistry, 1987, Holbrook, p. 80.*
Barreto et al, Carbohydrate Polymers, 2006, 64, 2006, 287-91.*
Yagi et al, Journal of Pharmaceutical Sciences, 1984, 73(1), 62-65.*
Mandal et al, Carbohydrate Research, 1980, 87, 249-56.*
Akiko Sasaki, et al., "Analysis of polysaccharides derived from Ochidaceae (*Odontioda Lavender Lace "Sylvan"*) plant", Abstract of the Annual Meeting of Japan Society for Bioscience, Biotechnology, and Agrochemistry 2009, Date of Issue: Mar. 5, 2009, p. 12 (2P0091A).
European Search Report issued in EP 09746438.2 dated Jun. 1, 2011.

* cited by examiner

Primary Examiner — Scarlett Goon
Assistant Examiner — Ganapathy Krishnan
(74) Attorney, Agent, or Firm — Sughrue Mion, PLLC (57) ABSTRACT

This invention relates to an extract obtained from a plant of the genus *Odontoglossum* of the family Orchidaceae, or from a plant derived from a hybrid plant of the genus *Odontoglossum* and the genus *Cochlioda*, to a method for preparing the extract, and to an external agent for skin comprising the extract.

8 Claims, 5 Drawing Sheets
(1 of 5 Drawing Sheet(s) Filed in Color)

EXTRACT OBTAINED FROM *ORCHIDACEAE* PLANTS, METHOD FOR PRODUCING THE EXTRACT, AND EXTERNAL AGENT FOR SKIN COMPRISING THE EXTRACT

CROSS REFERENCE TO RELATED APPLICATIONS

This application is a National Stage of International Application No. PCT/JP2009/056360 filed Mar. 27, 2009, which claims priority from Japanese Patent Application No. 2008-129943, filed May 16, 2008, the contents of all of which are incorporated herein by reference in their entirety.

TECHNICAL FIELD

The present invention relates to an extract obtained from plants of Orchidaceae, to a method for producing the extract, and to an external agent for skin comprising the extract.

BACKGROUND ART

Extracts obtained from plants of Orchidaceae have hitherto been used in cosmetics or the like, since such extracts have moisturizing effect, skin-conditioning effect, skin-whitening effect, anti-aging effect on the skin, or the like. For example, the following patent documents, i.e. JP-A-2007-008911, JP-A-2007-077079, JP-A-2006-282536, JP-A-2005-179219, JP-A-2004-067549, JP-A-2002-205933, JP-A-2002-003336, Japanese Patent No. 3526590, Japanese Patent No. 3090156, JP-A-H2-279618 (1990), and JP-A-S57-102809 (1982), disclose cosmetics, skin-moisturizing agents, and skin external agents containing extracts obtained from plants of Orchidaceae.

As plants of Orchidaceae used for obtaining extracts, the aforementioned patent documents disclose, for example, *Gymnadenia* (JP-A-2007-077079), *Cattleya* (JP-A-2006-282536, JP-A-2004-067549), *Calanthe*, *Phaius* (JP-A-2005-179219), *Bletilla striata*, *Cephalanthera falcata*, *Cremastra appendiculata*, *Cymbidium goeringii*, *Dactylorhiza aristata*, *Dendrobium moniliforme*, *Epipactis thunbergii*, *Galeola septentrionalis*, *Gastrodia elata*, *Neottia nidusavis*, *Orchis*, *Vanilla fragrans* (JP-A-2002-205933), *Cymbidium* (JP-A-2002-003336), *Dactylorhiza*, *Cephalanthera*, *Neottia*, *Epipactis* (Japanese Patent No. 3526590), *Phalaenopsis* (Japanese Patent No. 3090156), *Dendrobium*, *Cattleya*, *Cymbidium*, *Cymbidium goeringii* (JP-A-H2-279618 (1990)), and *Bletilla striata* (JP-A-S57-102809 (1982)).

It is said that 20,000 or more plant species of Orchidaceae exist, and the Orchidaceae family is the largest family of angiosperms, accounting for approximately 10% thereof. The area of distribution extends from the tropical region to the frozen region, and plants of Orchidaceae grow in every environment, except for extremely dry regions. Thus, such plants are very diversified in terms of ecological and morphological properties, and there are many theories regarding the lineages and classifications of plants of Orchidaceae ("Sekai no Chinran Kiran daizukan," Seibundo Shinkosha, Japan, 2006). Thus, plants of Orchidaceae that belong to the different genera differ from one another in terms of morphologies, such as flowers, leaves, stems, and roots. Also, it can be easily deduced that components of extracts therefrom differ from one another.

Examples of natural polysaccharides that are known to be used as moisturizing agents include polysaccharides derived from animals, such as hyaluronic acid, and polysaccharides derived from plants, such as quince, *Tremella fuciformis*, and aloe (FRAGRANCE JOURNAL, Japan, March 2005). Also, the patent documents mentioned above state that polysaccharides are contained in extracts obtained from plants of Orchidaceae; i.e., *Cymbidium* (JP-A-2002-003336), *Dendrobium*, *Cattleya*, *Cymbidium*, *Cymbidium goeringii* rhizomes (JP-A-H2-279618 (1990)), and *Bletilla striata* tubers (JP-A-S57-102809 (1982)), and they also state that such polysaccharides have moistening effects. It is generally known that a polysaccharide is composed of many monosaccharides linked via glycoside linkages, there are many types of polysaccharides, and natural polysaccharides differ from each other in terms of sugar compositions, structures, molecular weights, and the like, depending on their origins. For example, hyaluronic acid is a linear polysaccharide polymer composed of alternately linked N-acetylglucosamine and glucuronic acid, a *Tremella fuciformis* polysaccharide is an acidic heteropolysaccharide mainly composed of mannose, xylose, and glucuronic acid, a polysaccharide extracted from the quince epidermis is an acidic heteropolysaccharide in which arabinose, xylose, or uronic acid is linked (FRAGRANCE JOURNAL, Japan, March 2005), an aloe polysaccharide is a heteropolysaccharide comprising mannose, galactose, and glucose at 11:0.2:1 ("Modified Aloe barbadensis Polysaccharide with Immunoregulatory Activity," Plant Medica, 66, 152-156, 2000), and a polysaccharide extracted from *Bletilla striata* tubers (i.e., *Bletilla*-glucomannan) is a heteropolysaccharide comprising mannose and glucose at 3:1 ("Plant Mucilages. VIII. Isolation and Characterization of a Mucous Polysaccharide, "*Bletilla*-glucomannan," from *Bletilla striata* Tubers.," Chem. Pharm. Bull. 21 (12) 2667-2671, 1973). Regarding polysaccharides derived from the plants of Orchidaceae, there is no description other than *Bletilla*-glucomannan contained in tubers of *Bletilla striata*, and details thereof have not yet been elucidated.

In addition to the plants of Orchidaceae, ivory palm, guar, *Ceratonia siliqua*, tara, and the like are listed as plants containing large quantities of mannan compounds. It is known that mannan compounds contained in the extracts of mannan compounds are subjected to acidic hydrolysis from the above plants to produce mannose (JP-A-2000-70000).

DISCLOSURE OF THE INVENTION

Problem to be Solved by the Invention

The object of the present invention is to obtain an extract from plants belonging to Orchidaceae having a higher level of moisture-retaining effect or the like, and to provide a skin external agent comprising such extract.

Means for Solving the Problem

The present inventors have conducted intensive studies in order to attain the above object. As a result, the present inventors have now found that an extract obtained from plants that belong to particular genera of Orchidaceae has a higher level of moisturizing effect or the like, and this finding led to the completion of the present invention.

The present invention is summarized as follows.

[1] An extract obtained from a plant of the genus *Odontoglossum* of the family Orchidaceae, or a plant derived from a hybrid plant of the genus *Odontoglossum* and the genus *Cochlioda*, having the following features (1) to (4):

(1) the extract comprises sugar components, approximately 60% to 70% by weight of which is accounted for by polysaccharides;

(2) 90% or more of a constitutive sugar of the polysaccharides is mannose;

(3) mannose is linked via a β-1,4 glycosidic linkage; and (4) the extract has a moisturizing effect.

[2] The extract according to [1], which further has the following feature:

(1) a part of mannose molecules are branched at position 2, 3, or 6.

[3] The extract according to [1] or [2], which further has the following feature:

(1) the extract has an effect of increasing hyaluronic acid production, an effect of increasing ceramide production, and an effect of increasing type IV collagen production.

[4] The extract according to any one of [1] to [3], which further has the following feature:

(1) the extract suppresses production of lipid peroxide.

[5] The extract according to any one of [1] to [4], wherein the plant derived from a hybrid plant of the genus *Odontoglossum* and the genus *Cochlioda* is a plant of the genus *Odontioda*.

[6] The extract according to any one of [1] to [5], wherein the plant of the family Orchidaceae is a variety selected from the group consisting of Lavender Lace "Sylvan," Marie Noel "Velano," and Augres "Royal Sash."

[7] The extract according to any one of [1] to [6], wherein the plant material for extraction contains flowers.

[8] A method for preparing the extract according to any one of [1] to [7], comprising the following steps of:

mixing a plant portion containing flowers of a plant of the genus *Odontoglossum* of the family Orchidaceae, or a plant derived from a hybrid plant of the genus *Odontoglossum* and the genus *Cochlioda*, with a solvent containing water, a hydrophilic organic solvent or a mixture thereof;

heating and extracting the mixture of the plant portion and the solvent; and obtaining the extract.

[9] The method according to [8], wherein the heating and extracting step comprises heating at a temperature of 60° C. to 120° C. and then cooling to a temperature of 0° C. to 60° C., for extraction.

[10] The method according to [8] or [9], wherein the solvent is a mixture of water and 1,3-butylene glycol.

[11] The extract according to any one of [1] to [7], wherein the extract is obtained by the method according to any one of [8] to [10].

[12] An external agent for skin comprising the extract according to any one of [1] to [7] and [11] as an active ingredient.

[13] The external agent for skin according to [12], wherein it is used for a pharmaceutical or cosmetic.

Advantage of the Invention

The extract of the present invention has a higher level of viscosity and a higher level of moisturizing effects, such as a moisture-retaining effect, an effect of increasing moisture content of skin surface, an effect of increasing hyaluronic acid production, an effect of increasing ceramide production, and an effect of increasing type IV collagen production in the epidermal keratinocytes. The extract also suppresses production of lipid peroxide. The extract of the present invention can be used as an active ingredient for a skin external agent for skin (e.g., a moisturizing agent or cosmetics).

This description includes all or part of the contents as disclosed in the description and/or drawings of Japanese Patent Application No. 2008-129943, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODES FOR CARRYING OUT THE INVENTION (1) Plants Used for Obtaining Extract

The extract of the present invention can be obtained from a plant(s) of the genus *Odontoglossum* of the family Orchidaceae, or a hybrid(s) of *Odontoglossum* and *Cochlioda*. The term "hybrid of *Odontoglossum* and *Cochlioda*" refers to a plant whose ancestors are a plant of the genus *Odontoglossum* and a plant of the genus *Cochlioda*. In addition to plants of *Odontioda*, which are hybrids of two genera, i.e. *Odontoglossum* and *Cochliod*, such hybrids include plants which are produced by crossing of a hybrid of the two genera, i.e. *Odontoglossum* and *Cochlioda*, with one or more genera enabling crossing with *Odontoglossum*. may be used. In the present description, plants of Orchidaceae are classified in accordance with Phylogeny and Classification of the Orchid Family (written by Robert L. Dressler).

Plants of the genus *Odontoglossum* belong to the Oncidiinae subtribe of the Maxillarieae tribe in the Epidendrum subfamily, and they grow in moutainous regions in tropical and subtropical regions from Central to South America. Such plants are mid- to large-size epiphytic orchids and produce many flowers (Yamakei Color Meikan, Ran (orchid), Yamakei Publishers, Japan, 1996). Plants of the genus *Odontoglossum* used in the present invention include, but are not particularly limited to, for example the varieties Augres "Royal Sash" (variety registration number 10588 in accordance with the Japanese Plant Variety Protection and Seed Act), Harvengtence "Tutu" (variety registration number 10942 in accordance with the Japanese Plant Variety Protection and Seed Act), and Puccini "Rimo" (variety registration number 16093 in accordance with the Japanese Plant Variety Protection and Seed Act), with the variety Augres "Royal Sash" being particularly preferable.

Hybrids of *Odontoglossum* and *Cochlioda* include, but are not particularly limited to, a plant of the genus *Odontioda* and a plant of the genus *Wilsonara*, with a plant of the genus *Odontioda* being preferable.

The genus *Odontioda* is an artificial genus resulting from crossing two genera (i.e., *Odontoglossum* and *Cochlioda*), and many varieties thereof produce flowers of a large size and various colors (Yamakei Color Meikan, Ran (orchid), Yamakei Publishers., Japan, 1996). Plants of the genus *Odontioda* include hybrids of *Odontoglossum* and *Cochlioda*, hybrids of

*Odontioda* and *Odontoglossum*, hybrids of *Odontioda* and *Cochlioda*, and hybrids of *Odontioda* and *Odontioda*.

The genus *Wilsonara* is an artificial genus resulting from crossing three genera: *Odontoglossum, Cochlioda,* and *Oncidium*. Many varieties thereof have long scapes, are multiflorous, and are resistant to coldness (Yamakei Color Meikan, Ran (orchid), Yama-kei Publishers, Japan, 1996). Examples of plants of the genus *Wilsonara* include hybrids of *Odontioda* and *Oncidium, Odontioda* and *Odontocidium*, hybrids of *Odontioda* and *Wilsonara*, and hybrids of *Odontoglossum* and *Wilsonara*.

Examples of plants of the genus *Odontioda* include the varieties Lavender Lace "Sylvan" (variety registration number 11539 in accordance with the Japanese Plant Variety Protection and Seed Act), Marie Noel "Velano" (variety registration number 3740 in accordance with the Japanese Plant Variety Protection and Seed Act), Baiser "Aubigne," and Nichirei Strawberryfield "Orion Star" (variety registration number 10344 in accordance with the Japanese Plant Variety Protection and Seed Act). The varieties Lavender Lace "Sylvan"and Marie Noel "Velano" are particularly preferable.

Examples of plants of the genus *Wilsonara* include the varieties Nichirei Gold "Star Gazer" (variety registration number 15106 in accordance with the Japanese Plant Variety Protection and Seed Act) and Leucadia "Autumn Leaf" (variety registration number 14753 in accordance with the Japanese Plant Variety Protection and Seed Act).

Plants of the genus *Odontoglossum*, plants of the genus *Cochlioda*, plants of the genus *Odontioda*, and plants of the genus *Wilsonara* are different from the plants of Orchidaceae described in the above-mentioned patent documents (i.e., JP-A-2007-008911, JP-A-2007-077079, JP-A-2006-282536, JP-A-2005-179219, JP-A-2004-067549, JP-A-2002-205933, JP-A-2002-003336, Japanese Patent No. 3526590, Japanese Patent No. 3090156, JP-A-H2-279618 (1990), and JP-A-557-102809 (1982)) in terms of their genera and tribes and additionally plant distribution, morphology, etc.

(2) Extraction Method

The method for preparing the extract of the present invention comprises a step of mixing a plant portion containing flowers with a solvent consisting of water, a hydrophilic organic solvent or a mixture thereof, and heating and extracting the mixture of the plant portion and the solvent, and a step of obtaining the extract. Plants used for extraction may be fresh, semi-dried, dried, or lyophilized, preferably lyophilized. Further, plants may be adequately ground or cut or may be unchanged, with ground plants being preferable. Plant portions used as materials for extraction may be seeds, roots, stems, leaves, flowers, bulbs, or whole plants, preferably plant portions containing flowers, more preferably flowers alone. Plants of the above varieties may be used alone or in combinations of two or more.

As the solvent, water, a hydrophilic organic solvent, or a mixture thereof can be used. Use of a hydrophilic organic solvent is preferable since an extract with higher viscosity can be obtained. Specific examples of solvents include, but are not particularly limited to, pure water, purified water, alcohols such as methanol, ethanol, butanol, propylene glycol, glycerine, and 1,3-butylene glycol, acetone, tetrahydrofuran, acetonitrile, 1,4-dioxane, pyridine, dimethyl sulfoxide, N,N-dimethylformamide, and acetic acid. Preferred solvents are methanol, butanol, propylene glycol, glycerine, and 1,3-butylene glycol. A hydrophilic organic solvent may be used alone for extraction, but use of a mixture of a hydrophilic organic solvent and water is preferable. In such a case, the concentration of the hydrophilic organic solvent is preferably 10 vol % to 90 vol %, more preferably 20 vol % to 60 vol %, and further preferably 25 vol % to 35 vol %. Alternatively, two or more hydrophilic organic solvents may be mixed and used for extraction. For example, ethanol, 1,3-butylene glycol, and water may be mixed. The amount of a solvent(s) added to plants is, but not particularly limited, preferably 100 ml to 1000 ml, more preferably 200 ml to 600 ml per 100 g plant.

Solvents are added to plants and then heated for 30 seconds to 1 hour and preferably 10 to 15 minutes. Heating temperature is 60° C. to 120° C. and preferably 80° C. to 90° C. Thereafter, the mixture is cooled, preferably quenched, to 0° C. to 60° C. and preferably 20° C. to 30° C., for extraction. The extraction time after cooling is, but not particularly limited, 1 hour to 7 days and preferably 8 hours to 16 hours (or overnight). By heating and cooling the plants at the initial stage of extraction, extracts with higher viscosity can be obtained. The thus-obtained extracts exhibit good stability of viscosity with the elapse of time during storage. It is considered that enzymes or the like that degrade viscous components are contained in plants and are deactivated by heating. Further, extracts can be prevented from browning, and a color hue of light yellow to red can be maintained. (If flowers are employed, then the color of the flower reflects said color hue.)

After extraction, residues may be removed via filtration, centrifugation, or other means, where needed. Additionally, a step of concentration or purification may be performed. Such step can be performed via various known techniques, such as vacuum concentration, lyophilization, precipitation with the use of an ethanol solvent, various chromatography techniques, such as ion-exchange chromatography on DEAE column, gel filtration chromatography, and HPLC, and ultrafiltration.

(3) Extract

The extract obtained by the method (2) above comprises sugars, proteins, polyphenols, and the like, and it has a high viscosity. Main components of the solids in the extract are sugars, and approximately 60 wt % to 70 wt % or more of the sugar components are composed of polysaccharides. The sugar constituents of the extract comprise 40 wt % to 60 wt % mannose and 15 wt % to 25 wt % glucose when converted to monosaccharides. Fructose may be completely removed from the extract via further purifiation, and the extract may contain approximately 2 wt % to 5 wt % glucose. Where total constitutive sugars of polysaccharides contained in the extract is 100 wt %, then 90 wt % or more, preferably 95 wt % or more, and more preferably 97 wt % or more thereof is composed of mannose. The purified products of the polysaccharides (in Example 10 (iv), Example 21 (iv), and Example 22 (iv) as described below) comprise mannose and glucose, and the composition of them (by weight ratio) is preferably 90:10 to 99:1, and more preferably 95:5 to 98:2. And the purified products contain polysaccharide polymers comprising a large quantity of mannose molecules linked via β-1,4 glycoside linkages. A part of the mannose molecules are branched at position 2, 3, or 6.

The purified product of the extract has higher viscosity, but the viscosity is lowered upon enzyme degradation (by β-1,4-mannanase) (see Example 10). Thus, polysaccharides contained in the purified product are considered to contribute to the viscosity. The viscosity of the extract is 0.01 to 0.6 Pa·s (10 to 600 cP) for example, when measured using a sine-wave vibro viscometer at 25° C. The extract has moisturizing effects. Specifically, the extract has a moisture-retaining effect, an effect of increasing moisture content of skin surface, an effect of increasing hyaluronic acid production, an effect of promoting ceramide production, and an effect of promoting type IV collagen production in epidermal keratinocytes. Further, the extract suppresses production of lipid peroxide. Such biological effects (or actions) are verified in the examples below. Also, cosmetics comprising such extract are free of stickiness or tautness and sufficiently penetrate skin.

(4) External Agent for Skin

The external agent for skin of the present invention is not particularly limited in respect of its applications, as long as it is in a dosage form that can be applied to the skin for use in pharmaceuticals or cosmetics such as moisturizing agents and cosmetic agents. Examples of dosage forms include creams, gels, liquids, suspensions, powders, foams, and solids. Specific examples include hand cream, lotion, emulsion, beauty essence, face cream, cleansing cream, facial soap, facial mask, shaving foam, suntan cream, suntan lotion, sunblock cream, sun-block lotion, makeup base, foundation, face powder, powder, lipstick, lip cream, eye liner, eye cream, eye shadow, eyelash liner, shampoo, rinse, conditioner, hair dye, body-wash, and body lotion.

The content of the extract of the present invention in the external agent for skin is preferably 0.0001 wt % to 25 wt %, and more preferably 0.1 wt % to 15 wt %. In addition to the extract, various components usable in the external agent for skin, such as a moisturizing agent, a skin-whitening agent, an antioxidant, a thickener, an oil component, an antibacterial agent, an emulsifier, and an ultraviolet absorber, can be optionally added to the external agent for skin. Examples of moisturizing agents include: a mucopolysaccharide(s), such as hyaluronic acid or chondroitin sulfate, or a derivative(s) thereof; a protein(s), such as collagen, elastin, or keratin, or a derivative(s) thereof; an amino acid(s), such as glycine, serine, aspartic acid, glutamic acid, or arginine, or a derivative(s) thereof; a sugar(s), such as sorbitol, trehalose, glucose, or sucrose; urea; phospholipid; ceramide; a plant extract(s), such as an aloe extract or a quince extract; and a polyhydric alcohol(s), such as glycerine, propylene glycol, or polyethylene glycol. Examples of skin-whitening agents include vitamin C and derivatives thereof, vitamin E and derivatives thereof, vitamin A and derivatives thereof, glycyrphosphate and derivatives thereof, glycyrrhizin and derivatives thereof, niacinamide, arbutin, kojic acid, ellagic acid, linolic acid, tranexamic acid, placenta extract, and plant extracts, such as camomile extract, scutellaria extract, grape extract, acelora extract, Camu Camu extract, and Camu Camu seed extract. Examples of antioxidants include superoxide dismutase, mannitol, quercetin, catechin, astaxanthin, vitamin A, vitamin B, vitamin E, dibutylhydroxytoluene, butylhydroxyanisole, coenzyme Q10, α-lipoic acid, and a plant extract such as acelora seed extract. Examples of thickeners include a naturally occurring polymers, such as carragheenan, pectin, agar, gum Arabic, guar gum, Locust bean gum, xanthan gum, quince seeds, gelatin, and starch, cellulosic polymers, such as methylcellulose and hydroxycellulose, an acrylic acid polymer such as carboxyvinyl polymer, an alginic acid polymer such as sodium alginate, and alcohols, such as cetostearyl alcohol and behenyl alcohol. Examples of oil components include squalane, jojoba oil, castor oil, safflower oil, and olive oil. Examples of antibacterial agents include methyl parahydroxybenzoate, ethyl parahydroxybenzoate, propyl parahydroxybenzoate, butyl parahydroxybenzoate, sorbic acid, dehydrobutyric acid, and phenoxyethanol. Examples of emulsifiers include glyceryl monostearate, potassium hydroxide, and stearic acid. Examples of ultraviolet absorbers include a p-aminobenzoic acid ultraviolet absorber, a salicylic acid ultraviolet absorber, a cinnamic acid ultraviolet absorber, an anthranilic acid ultraviolet absorber, and a benzophenone ultraviolet absorber.

Further, a surfactant, a chelating agent, a dye, a pH modifier, a fragrance, an algefacient, a blood flow accelerator, a keratolytic agent, an astringent, a wound-healing agent, a foaming agent, an antiallergic agent, or a cell activator, may be added.

Hereafter, the present invention is described with reference to the examples, although the present invention is not limited thereto.

EXAMPLES

Example 1

Method for Preparing Extract (1)

Flowers of the *Odontioda* Lavender Lace "Sylvan" (100 g) were frozen in a freezer (Medical Freezer, SANYO) at −40° C. for 1 week or longer, lyophilized in a freeze-drier (Freeze-Dryer, TRIO SCIENCE CO., LTD.) for 4 days, and ground using the Labo Milser (Iwatani Corporation). After addition of an aqueous solution of 30 vol % 1,3-butylene glycol (500 ml), the mixture was subjected to agitation and extraction at 80° C. to 90° C. for 10 minutes, and then immediately cooled, followed by agitation and extraction at 25° C. overnight. Following filtration, the extract was obtained in the amount of 400 ml (solid concentration: 1.4 wt %).

Example 2

Method for Preparing Extract (2)

An extract (400 ml) (solid concentration: 0.55 wt %) was obtained in the same manner as in Example 1, except that the whole plant (flower, stem, leaf, root, and bulb) (111 g) of the *Odontioda* Lavender Lace "Sylvan" was used and 555 ml of an aqueous solution of 30 vol % 1,3-butylene glycol was added.

Example 3

Method for Preparing Extract (3)

An extract (400 ml) (solid concentration: 1.1 wt %) was obtained in the same manner as in Example 1, except that 100 g of flowers of the *Odontoglossum* Augres "Royal Sash" was used.

Example 4

Method for Preparing Extract (4)

An extract (400 ml) (solid concentration: 0.60 wt %) was obtained in the same manner as in Example 1, except that the whole plant (flower, stem, leaf, root, and bulb) (93.5 g) of the *Odontoglossum* Augres "Royal Sash" was used and 467 ml of an aqueous solution of 30 vol % 1,3-butylene glycol was added.

Example 5

Method for Preparing Extract (5)

An extract (400 ml) (solid concentration: 1.1 wt %) was obtained in the same manner as in Example 1, except that 100 g of flowers of the *Odontioda* Marie Noel "Velano" was used.

Example 6

Method for Preparing Extract (6)

An extract (400 ml) (solid concentration: 0.73 wt %) was obtained in the same manner as in Example 1, except that the whole plant (flower, stem, leaf, root, and bulb) (101 g) of the *Odontioda* Marie Noel "Velano" was used and 505 ml of an aqueous solution of 30 vol % 1,3-butylene glycol was added.

Example 7

Viscosity Measurement

Viscosity of the extracts prepared in the manner described in Example 1, Example 3, and Example 5 at 25° C. was measured using a sine-wave vibro viscometer SV-10 (A & D). A solvent of the extract (an aqueous solution of 30 vol % 1,3-butylene glycol) was used as the control. For comparison, a hot-water extract of *Bletilla striata* tubers, which is known to contain a mucilage(glucomannan), was prepared by the method described in the examples of the Patent Document 11 (JP-A-57-102809 (1982)). This extract was diluted to 1 wt % in 30 vol % 1,3-butylene glycol, in order to obtain the same conditions as the examples in terms of solid concentration, solvent type, and solvent concentration. The results are shown in Table 1. Viscosity of the extracts of Examples 1, 3, and 5 was found to be 5 times as high or higher than that of the *Bletilla striata* tubers extract. Further, the extracts of Examples 1, 3, and 5 were found to sufficiently penetrate skin and found to be free of stickiness or tautness.

TABLE 1

| | Viscosity Pa·s (cP) |
|---|---|
| Lavender Lace "Sylvan" flower extract (Example 1) | 0.0986 (98.6) |
| Augres "Royal Sash" flower extract (Example 3) | 0.0446 (44.6) |
| Marie Noel "Velano" flower extract (Example 5) | 0.0499 (49.9) |
| *Bletilla striata* tubers extract | 0.00909 (9.09) |
| Control (30% 1,3-butylene glycol) | 0.00391 (3.91) |

Example 8

Component Analysis of Lavender Lace "Sylvan" Flower Extract Obtained in Example 1

In order to clarify components of the extract prepared by the method of Example 1, sugar content, polyphenol content, and protein content were measured. The test methods and results are shown below.
(i) Measurement of Sugar Content (by Phenol-Sulfuric Acid Method)
[Test Method and Results]
To 500 µl of the solution of the extract diluted 500-fold with distilled water 500 µl of an aqueous solution of 4 vol % phenol was added. And then 2.5 ml of conc $H_2SO_4$ was speedily added dropwise, and the mixture was agitated. The products were cooled in a water bath for 5 minutes and then heated at 30° C. for 10 minutes. The absorbance was measured at 485 nm. A calibration curve was made using a glucose standard solution to determine the total amount of sugars in the extract. Sugar content in the extract was 12,323 µg/ml, and approximately 88 wt % of the solid components (1.4 wt %) was sugars.
(ii) Measurement of Polyphenol Content (by Folin-Denis Method)
[Test Method and Results]
The solution of the extract 1 diluted 6-fold with distilled water (80 ml) was purified using the C18 column (Sep-Pak Vac 35 cc C18 Cartridge: Waters) to obtain 28.9 mg dry matter of the adsorbed component. The dry matter was dissolved in an aqueous solution of 50 vol % methanol to adjust the solid content to 1 wt %, and the resultant solution was diluted 100-fold with distilled water to prepare a sample for measurement. To 200 µl of the sample, 3.2 ml of distilled water and 200 µl of Folin-Ciocalteu's phenol reagent (Merck) were added, the mixture was agitated, 400 µl of an aqueous solution of saturated sodium carbonate was added thereto, the mixture was agitated, the resultant was allowed to stand for 60 minutes, and the absorbance was measured at 700 nm. A blank test was carried out by adding distilled water instead of Folin-Ciocalteu's phenol reagent. A calibration curve was made using a catechin standard solution to determine the polyphenol content in the sample, and the polyphenol content in the extract was then determined. The extract was found to contain polyphenol at 0.1 mg/ml, and approximately 1 wt % of the solid components (1.4 wt %) was found to be polyphenol.
(iii) Measurement of Protein Content (by Lowry Method)
Protein content was measured using the DC Protein assay kit (Bio Rad Laboratories). To 200 µl of the solution of the extract diluted 7-fold with an aqueous solution of 30 vol % 1,3-butylene glycol, 100 µl of Reagent A was added, the mixture was agitated, 800 µl of Reagent B was added thereto, the mixture was agitated, the resultant was allowed to stand for 15 minutes, and the absorbance was determined at 750 nm. A calibration curve was prepared using a BSA standard solution to determine the protein content in the extract. The extract was found to contain a protein at 1,529.0 µg/ml, and approximately 10 wt % of the solid content (1.4 wt %) was found to be proteins.

The results of the above analysis demonstrate that the main component of the extract is sugars and the extract contains proteins and polyphenol as other components.

Example 9

Analysis of Sugar Composition in the Lavender Lace "Sylvan" Flower Extract Obtained in Example 1

In order to clarify the kind of sugars which are main components of the extract, the composition of sugars in the extract prepared by the method of Example 1 was analyzed. Analysis was carried out by two methods; i.e., a method for measuring sugar components with degradation and a method for measuring only free sugars without degradation. The test methods and results are shown below.
(i) Analysis Via Degradation Treatment
[Sample Preparation]
The extract (40 µl) was dried under reduced pressure, 200 µl of an aqueous solution of 2 mol/l trifluoroacetic acid was added thereto, and the extract was hydrolyzed in a vacuum sealed tube at 100° C. for 6 hours, and then dried again under reduced pressure. The dry matter was dissolved in 200 µl of distilled water and filtered through a 0.22 µm filter.
[Method for Measuring Neutral Sugars]
The prepared sample was measured using the HPLC system (LC-9A system: Shimadzu Corporation, Japan). Conditions for measurement are shown below.
Column: TSK-gel Sugar AXG 15 cm×4.6 mm (I.D.) (Tosoh Corporation, Japan)
Column temperature: 70° C.
Mobile phase: 0.5M potassium borate buffer, pH 8.7
Mobile phase flow rate: 0.4 ml/min
Reaction reagent: 1% arginine/3% boric acid
Reaction reagent flow rate: 0.5 ml/min
Reaction temperature: 150° C.

Detector: spectrophotofluorometer RF-10A$_{XL}$ (Shimadzu Corporation, Japan)
Detection wavelength: Ex.=320 nm, Em.=430 nm
Calibration curves were made using standard solutions of rhamnose, ribose, mannose, fructose, arabinose, galactose, xylose, glucose, and sucrose. The results are shown in Table 2.
[Method for Measuring Acidic Sugars]
The prepared sample was measured using the HPLC system (LC-9A system: Shimadzu Corporation, Japan). Conditions for measurement are shown below.
Column: Shimpack ISA-07 25 cm×4.6 mm (I.D.) (Shimadzu Corporation, Japan)
Column temperature: 70° C.
Mobile phase: 1M potassium borate buffer, pH 8.7
Mobile phase flow rate: 0.8 ml/min
Reaction reagent: 1% arginine/3% boric acid
Reaction reagent flow rate: 0.8 ml/min
Reaction temperature: 150° C.
Detector: spectrophotofluorometer RF-10A$_{XL}$ (Shimadzu Corporation, Japan)
Detection wavelength: Ex.=320 nm, Em.=430 nm
Calibration curves were made using standard solutions of galacturonic acid, iduronic acid, and glucuronic acid. The results are shown in Table 2.

TABLE 2

|  | (µg/ml) |
| --- | --- |
| Man | 5198.92 |
| Glu | 1426.29 |
| GalA | 117.04 |
| Xyl | 114.14 |
| Gal | 59.86 |
| Ara | 44.57 |
| Rha | 37.96 |
| Rib | 5.03 |
| Total | 7003.81 |

Man: mannose,
Glu: glucose,
GalA: galacturonic acid,
Xyl: xylose,
Gal: galactose,
Ara: arabinose,
Rha: rhamnose,
Rib: ribose (ii) Analysis of Free Sugars
[Sample Preparation]
The solution of the extract diluted 10-fold with distilled water (200 µl) was filtered through a 0.22-µm filter.
[Method for Measuring Neutral Sugars]
The prepared sample was measured using the HPLC system (LC-9A system: Shimadzu Corporation, Japan). Conditions for measurement are shown below.
Column: TSK-gel Sugar AXG 15 cm×4.6 mm (I.D.) (Tosoh Corporation, Japan)
Column temperature: 70° C.
Mobile phase: 0.5M potassium borate buffer, pH 8.7
Mobile phase flow rate: 0.4 ml/min
Reaction reagent: 1% arginine/3% boric acid
Reaction reagent flow rate: 0.5 ml/min
Reaction temperature: 150° C.
Detector: spectrophotofluorometer RF-10A$_{XL}$ (Shimadzu Corporation, Japan)
Detection wavelength: Ex.=320 nm, Em.=430 nm
Calibration curves were prepared using standard solutions of rhamnose, ribose, mannose, fructose, arabinose, galactose, xylose, glucose, and sucrose. The results are shown in Table 3.

TABLE 3

|  | (µg/ml) |
| --- | --- |
| Fru | 1754.83 |
| Glu | 1275.63 |
| Suc | 330.48 |
| Xyl | 23.66 |
| Man | 22.19 |
| Gal | 19.97 |
| Total | 3426.76 |

Fru: fructose,
Glu: glucose,
Suc: sucrose,
Xyl: xylose,
Man: mannose,
Gal: galactose As shown in Table 2 and in Table 3, the extract obtained by the method of Example 1 was found to contain monosaccharides such as fructose and glucose, and polysaccharides containing mannose in rich, and a half or more of the extract was found to be accounted for by such polysaccharides. Since the content of mannose as a free sugar was low, mannose was considered to be a constitutive sugar of polysaccharides.

Example 10

Analysis of Polysaccharide Contained in the Purified Product from the Lavender Lace "Sylvan" Flower Extract Obtained in Example 1

In order to study the composition and structure of a polysaccharide as a main component of the extract, a polysaccharide was separated and purified from the extract prepared by the method of Example 1, and sugar composition analysis and enzyme degradation were carried out. The test method and results are shown below.
(i) Crude Fractionation (by Ethanol Precipitation)
Ethanol (1200 g) was added to the extract (300 g) prepared by the method of Example 1 to prepare an aqueous solution of 80 wt % ethanol. Thus obtained solution was allowed to stand at 7° C. overnight, the precipitate and the supernatant were separated via centrifugation, and the precipitate was dried using a freeze-dryer. The supernatant was concentrated using a rotary evaporator, ethanol was added again, and a similar procedure was carried out. Thus, 3.7 g of an ethanol precipitate was obtained by these procedures.
(ii) Crude Fractionation (by C18 Column Treatment)
The ethanol precipitate (3.7 g) prepared in (i) above was dissolved in water to prepare an aqueous solution of 1 wt %, and the resulting solution was allowed to pass through a column (3 cm×100 cm) filled with a reversed-phase resin (YMC-GEL, ODS-A120-S150: YMC) to remove impurities that had adsorbed to the column. The fraction that had passed through the column was concentrated using a rotary evaporator, and ethanol precipitation was carried out in the same manner as in (i) above to recover an ethanol precipitate (1.8 g).
(iii) Separation and Purification (by DEAE Column Treatment)
The ethanol precipitate prepared in (ii) above was dissolved in distilled water to prepare an aqueous solution of 2 wt %, 5 ml thereof was allowed to pass through the column (3 cm×100 cm) filled with ion exchange resin (DEAE sepharose CL-6B: Amersham Pharmacia Biotech AB), and a sugar-containing fraction was eluted with distilled water and 0.5M NaCl for fractionation. The obtained fraction was concentrated 10-fold using a ultrafiltration membrane having a molecular weight cut off of 5,000 (Amicom Ultra, Ultracel-10K: MILLIPORE) and a colorless solution having very high viscosity was obtained. This solution was lyophilized to obtain 52.7 mg of a white purified product.

(iv) Sugar Composition Analysis

The purified product obtained in (iii) above was dissolved in distilled water to prepare an aqueous solution of 1 wt %, and sugar composition analysis was carried out.

[Sample Preparation]

An aqueous solution of 5 mol/l trifluoroacetic acid (200 μl) was added to 100 μl of a 1 wt % aqueous solution, the solution was subjected to hydrolysis at 120° C. for 3 hours, and then dried under reduced pressure. The sample obtained by dissolving the dry product in 500 μl of distilled water and the sample diluted 10-fold with distilled water were filtered through a 0.22-μm filter.

[Method for Measuring Neutral Sugars]

The prepared sample was measured using the HPLC system (LC-9A system: Shimadzu Corporation, Japan). Assay conditions are shown below.

Column: TSK-gel Sugar AXG 15 cm×4.6 mm (I.D.) (Tosoh Corporation, Japan)
Column temperature: 70° C.
Mobile phase: 0.5M potassium borate buffer, pH 8.7
Mobile phase flow rate: 0.5 ml/min
Reaction reagent: 1% arginine/3% boric acid
Reaction reagent flow rate: 0.5 ml/min
Reaction temperature: 150° C.
Detector: spectrophotofluorometer RF-10A$_{XL}$ (Shimadzu Corporation, Japan)
Detection wavelength: Ex.=320 nm, Em.=430 nm Calibration curves were prepared using standard solutions of rhamnose, ribose, mannose, fructose, arabinose, galactose, xylose, glucose, and sucrose, and sugar contents of the purified product were determined.

The results of polysaccharide analysis are shown in Table 4. The purified product contained mannose and glucose. Table 4 shows the ratio of mannose to glucose (by weight ratio, %). The weight ratio of mannose to glucose was about 98:2.

TABLE 4

|  | (μg/ml) | Percentage (%) |
| --- | --- | --- |
| Man | 945.54 | 98.1 |
| Glu | 18.74 | 1.9 |
| Total | 964.28 | 100 |

Man: mannose,
Glu: glucose (v) Enzyme Degradation

To an aqueous solution of 1 wt % purified product prepared in (iv) above and the extract prepared by the method of Example 1, β-1,4-mannanase (Yakult Pharmaceutical Industry Co., Ltd., Japan) and 0.2M phosphate buffer (pH 6.8) were added, the resultant was allowed to stand at 50° C. overnight, and the enzyme degradation reaction was then carried out. After the reaction, the enzyme was inactivated by heating at 90° C. for 10 minutes, and sugar composition analysis was carried out under the same conditions as in Example 9-(ii).

As a result of analysis, mannose released via enzyme degradation was detected. Thus, it was found that the polysaccharides contained polysaccharides which are composed of mannose molecules linked via β-1,4 glycoside linkages. Since viscosity of the solution and the extract was significantly decreased, a polysaccharide was found to contribute to the viscosity.

Example 11

Assay for Suppressing Production of Lipid Peroxide

The effect of the extract on suppression of lipid peroxide production was evaluated by the suppression test of autoxidation of linolic acid. Lipid peroxide was evaluated by the ferric thiocyanate method. The assay method and the results are shown below.

[Sample Preparation]

To 2 ml of the solution of 2.5 wt % linolic acid in ethanol, 4 ml of 0.5M phosphate buffer (pH 7.0), 2 ml of ethanol, and 2 ml of the extract prepared by the method of Example 1, which was diluted to 0.02 wt % in 3 vol % 1,3-butylene glycol (as a solvent), were added and mixed, and the resulting mixture was stored in a brown bottle at 40° C. The sample stored at 4° C. was employed as a blank sample. Also, a sample prepared by adding 3 vol % 1,3-butylene glycol was employed as a control sample.

[Assay Method and Results]

Figure 1:
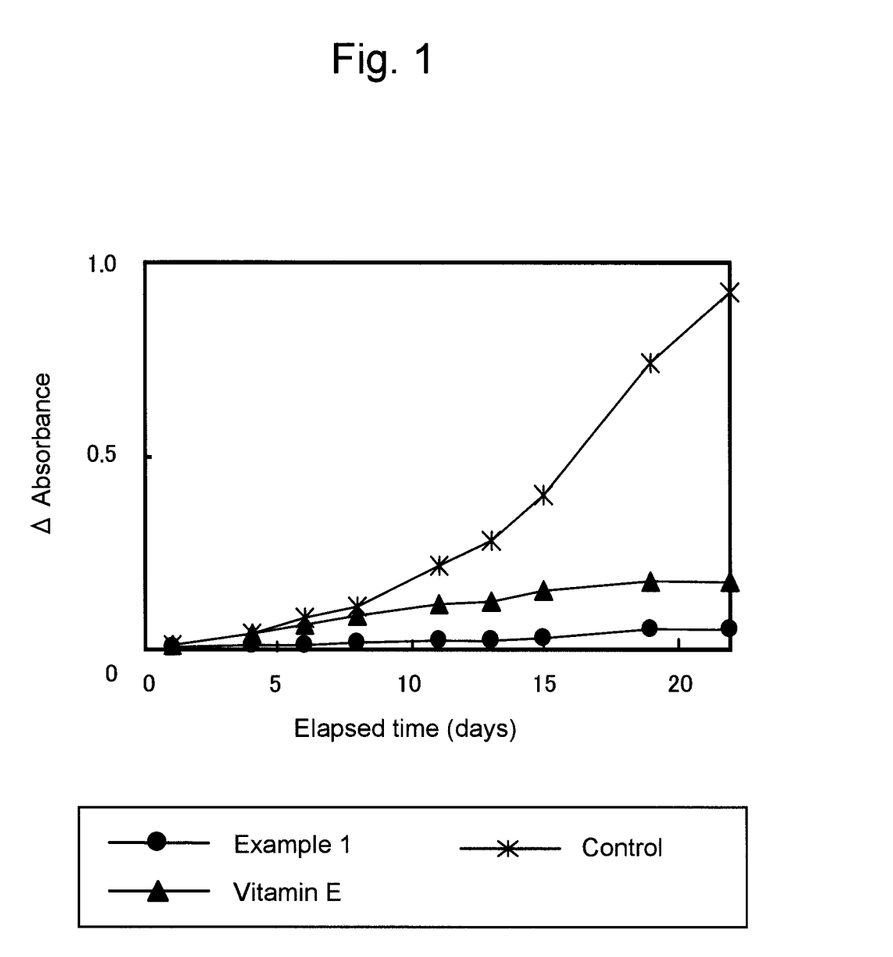
FIG. 1 shows the effect of suppressing production of lipid peroxide in Example 11.

To 0.1 ml of the sample, 9.7 ml of ethanol, 0.1 ml of an aqueous solution of 30 wt % ammonium thiocyanate solution, and 0.1 ml of an aqueous solution of 20 mM ferrous chloride were added, and the absorbance at 500 nm was measured 3 minutes later. The Δ absorbance was determined by subtracting the absorbance of the blank, and the amount of lipid peroxide was evaluated. For comparison, vitamin E (0.02 wt %), which is commonly used as an antioxidant, was used. The results are shown in FIG. 1. The sample suppressed production of lipid peroxide equivalent to or stronger than vitamin E, and persistence of the effect was observed.

Example 12

Test for Moisture Retention (1)

The capacity of the extract for moisture retention was evaluated. The test method and the results are shown below.

[Test Method and Results]

The extracts prepared by the methods of Example 1, Example 3, and Example 5 were diluted to 1 wt % with an aqueous solution of 30 vol % 1,3-butylene glycol, and the resulting solutions were employed as test samples. The test sample (10 μg) was applied to a 1 cm×1 cm filter paper (FILTER PAPER 5B (ADVANTEC TOYO)) and measured weight at 22° C. and at 30% RH with the elapse of time. A solvent of the extract (i.e., an aqueous solution of 30 vol % 1,3-butylene glycol) was employed as a control. For comparison, hot-water extract of *Bletilla striata* tubers (JP-A-S57-102809 (1982)), 50% ethanol extract of the whole *Cymbidium* plant (JP-A-2002-3336), and hot-water extract of *Phalaenopsis* flower (JP-A-H5-70338 (1993)), which, among the extracts of the plants of Orchidaceae, are known to have moisture-retaining effect were prepared by the extraction methods described in the examples of the relevant patent publications. These extracts were diluted to 1 wt % in 30 vol % 1,3-butylene glycol (as a solvent), in order to have the same conditions among examples in terms of solid concentration, solvent type, and solvent concentration. When the extraction solvents used in the examples were different from those used for comparison, the latter extraction solvents were removed using an evaporator (a rotary evaporator, EYELA) to prepare samples.

Figure 2:
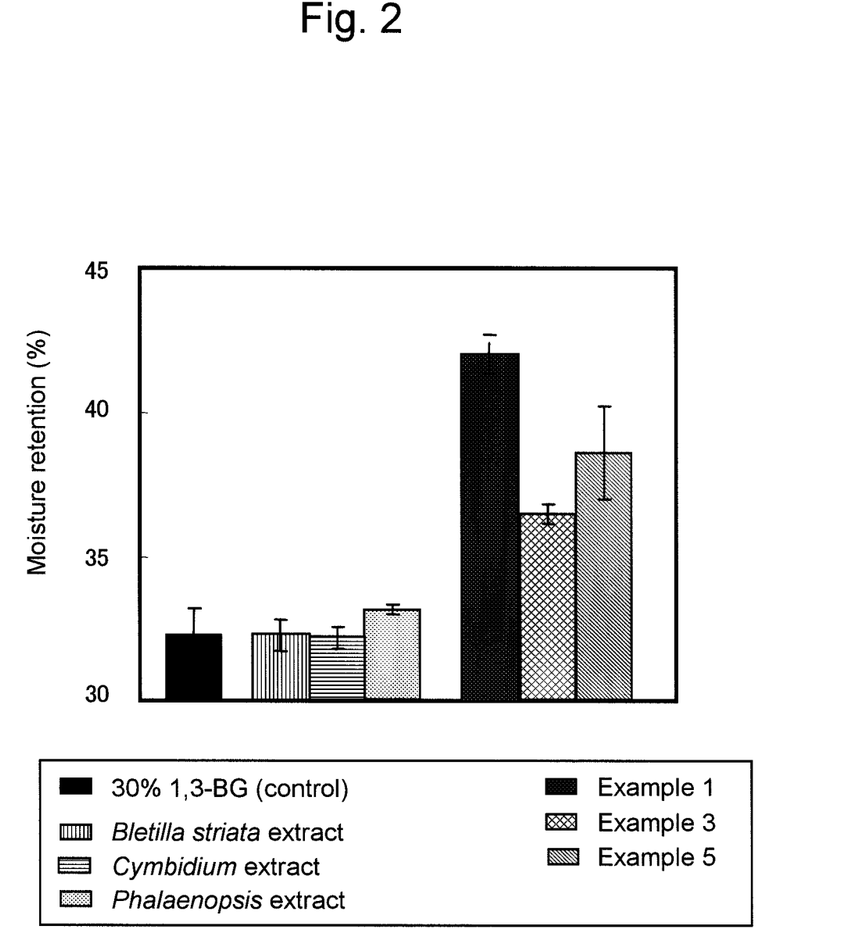
FIG. 2 shows the effect of moisture retention by Test (1) in Example 12.

The results are shown in FIG. 2. Numerical values represent the percentage of moisture retention, which was determined by considering the weight at the initiation of test as 100%. FIG. 2 shows the percentage of moisture retention at 15 minutes after the initiation of test.

Compared with the extracts used for comparison, the extracts prepared by the methods of Example 1, Example 3, and Example 5 were found to have higher moisture-retaining effect (FIG. 2).

Example 13

Test for Moisture Retention (2)

The capacity of the polysaccharide for moisture retention was evaluated. The test method and the results are shown below.
[Test Method and Results]
The purified product obtained in Example 10-(iii) was diluted to 1 wt % with distilled water and the resultant was employed as a test sample. The test sample (10 μg) was applied to a 1 cm×1 cm filter paper (FILTER PAPER 5B (ADVANTEC TOYO)) and measured weight at 22° C. and at 30% RH with the elapse of time. Distilled water was used as a control. For comparison, hyaluronic acid (Kibun. Food Chemifa Co., Ltd.), which has been extensively used as a cosmetic ingredient for moisturizing cosmetics, was diluted to 1 wt % with distilled water.

Figure 3:
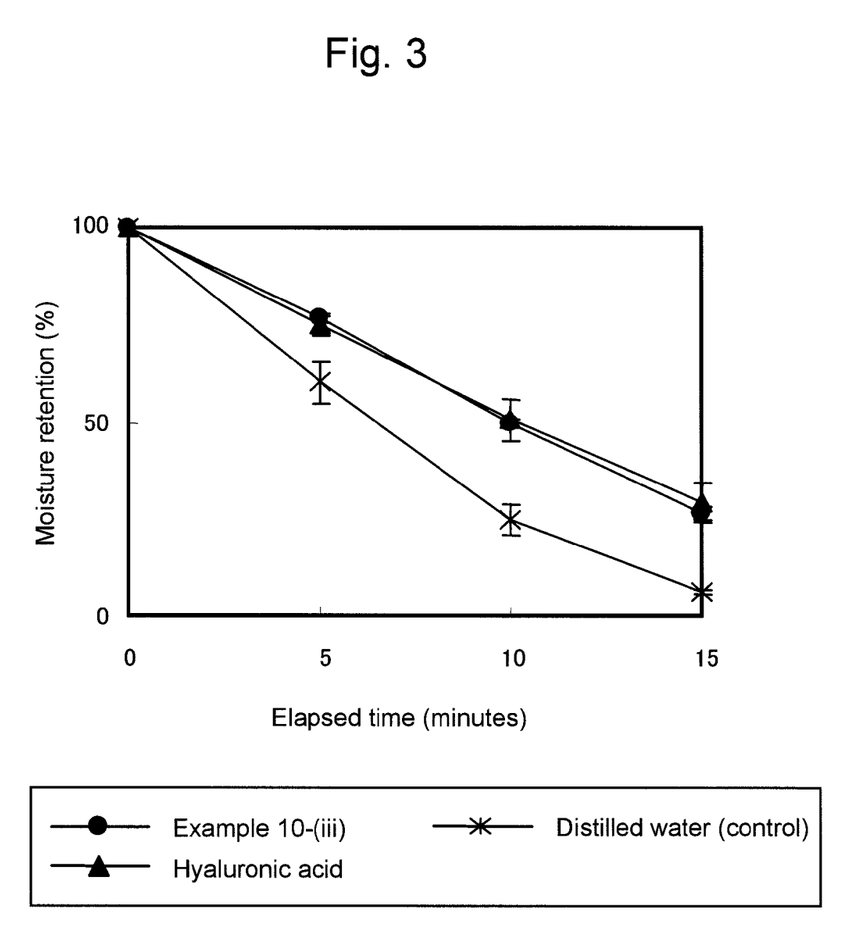
FIG. 3 shows the effect of moisture retention by Test (2) in Example 13.

The results are shown in FIG. 3. Numerical values represent the percentage of moisture retention, which was determined by considering the weight at the initiation of test as 100%. FIG. 3 shows percentage of moisture retention at 15 minutes after the initiation of test.

Compared with the control, the purified product obtained in Example 10-(iii) was found to have significantly higher moisture retaining effect. Moisture-retaining properties that were equivalent to or higher than those of hyaluronic acid, which is known to have high moisture-retaining properties, were observed.

Example 14

Test for Moisture-Retaining Properties

To evaluate moisture-retaining properties of the extracts, moisture content of skin surface was measured with the elapse of time. Moisture content of skin surface was evaluated for skin conductance. The test method and the results are shown below.
[Test Method and Results]
Assay instrument: SKICON-200EX (I.B.S. Ltd, Japan)
Test environment: 20 to 22° C., 30 to 40% RH After the panels (healthy adults; N=3) entered the laboratory, they were requested to wash the test regions with a soap containing no moisturizing components, they were requested to rest for 20 minutes, and they were then subjected to measurement. After the initial value at the medial side of the forearm was measured, the extracts prepared by the methods of Example 1, Example 3, and Example 5 were applied thereto at 10 nl/4 cm$^2$, and moisture content of skin surface was measured with the elapse of time. An aqueous solution of 30 vol % 1,3-butylene glycol was used as a control. For comparison, hot-water extract of *Bletilla striata* tubers (JP-A-S57-102809 (1982)), 50% ethanol extract of the whole *Cymbidium* plant (JP-A-2002-3336), and hot-water extract of *Phalaenopsis* flower (JP-A-H5-70338 (1993)), which, among the extracts of the plants of Orchidaceae, are known to have moisture-retaining effect, were prepared by the extraction methods described in the examples of the relevant patent publications. These extracts were diluted to 1 wt % in 30 vol % 1,3-butylene glycol (as a solvent), in order to have the same conditions among the examples in terms of solid concentration, solvent type, and solvent concentration. When the extraction solvents used in the examples were different from those used for comparison, the latter extraction solvents were removed using an evaporator (a rotary evaporator, EYELA) to prepare samples. Also, hyaluronic acid (Kibun. Food Chemifa Co., Ltd.), which has been extensively used as a cosmetic ingredient having moisture-rich for cosmetics, was diluted to 1 wt % with 30 vol % 1,3-butylene glycol, and used for comparison.

Figure 4:
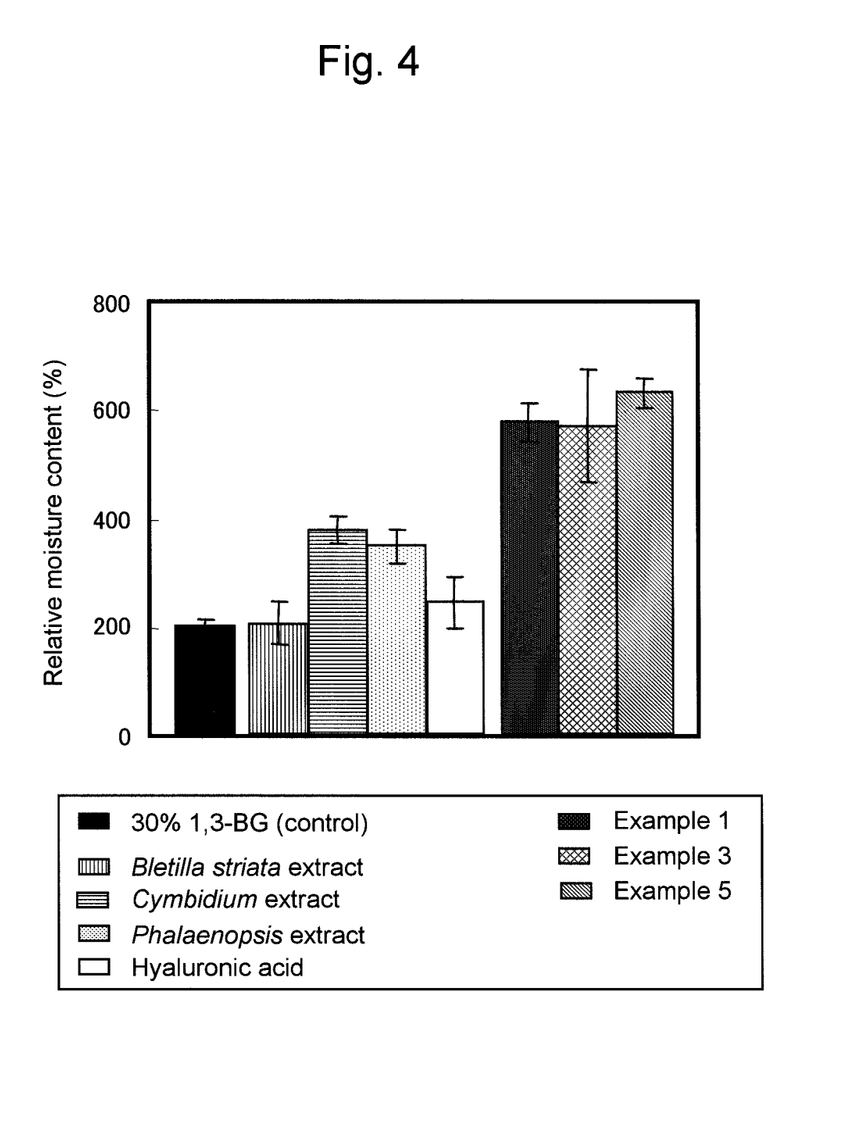
FIG. 4 shows the effect of increasing moisture content of skin surface in Example 14.

The results are shown in FIG. 4. Numerical values represent moisture contents relative to the initial value 100%. FIG. 4 shows the moisture contents at 60 minutes after the initiation of test.

Via application of the extracts prepared by the methods of Example 1, Example 3, and Example 5, moisture content was increased, and moisture-retaining effect was sustained for a long period of time. Since this effect was superior to those attained when other comparative extracts (e.g., *Bletilla striata* extract, *Cymbidium* extract, and *Phalaenopsis* extract) or moisturizing agent (hyaluronic acid) were applied, the extracts prepared by the methods of Example 1, Example 3, and Example 5 were found to have a higher moisturizing effect and to be effective as moisturizing agents.

Example 15

Formulation for Cosmetics

Based on formulation examples shown below, a lotion, an emulsion and a cream, which contain the extract obtained by the method of Example 1, were prepared in accordance with conventional techniques. Also, placebo was prepared in the same manner, except that the extract was excluded therefrom. The unit indicates wt %.

| [Lotion] | |
|---|---|
| Purified water | 81.9 |
| Extract (Example 1) | 10.0 |
| 1,3-Butylene glycol | 3.0 |
| conc. glycerin | 2.0 |
| Dehydrated ethanol | 2.0 |
| Polyethylene glycol 1540 | 0.5 |
| Phenoxyethanol | 0.35 |
| Methyl parahydroxybenzoate | 0.15 |
| Xanthan gum | 0.1 |
| [Emulsion] | |
| Purified water | 77.04 |
| Extract (Example 1) | 10.0 |
| Squalane | 3.0 |
| 1,3-Butylene glycol | 3.0 |
| Cetostearyl alcohol | 3.0 |
| conc. glycerin | 2.0 |
| Glyceryl monostearate | 1.2 |
| Carboxyvinyl polymer | 0.3 |
| Xanthan gum | 0.15 |
| Methyl parahydroxybenzoate | 0.15 |
| Potassium hydroxide | 0.12 |
| Propyl parahydroxybenzoate | 0.03 |
| Natural vitamin E | 0.01 |
| [Cream] | |
| Purified water | 60.13 |
| Squalane | 15.0 |
| Extract (Example 1) | 10.0 |
| Stearic acid | 4.0 |
| 1,3-Butylene glycol | 3.0 |
| Cetostearyl alcohol | 3.0 |
| Behenyl alcohol | 2.0 |
| Glyceryl monostearate | 2.0 |
| Methyl polysiloxane | 0.5 |
| Methyl parahydroxybenzoate | 0.17 |
| L-arginine | 0.1 |
| Propyl parahydroxybenzoate | 0.05 |
| Natural vitamin E | 0.05 |

17

-continued

[Placebo lotion]

| | |
|---|---|
| Purified water | 88.9 |
| 1,3-Butylene glycol | 6.0 |
| conc. glycerin | 2.0 |
| Dehydrated ethanol | 2.0 |
| Polyethylene glycol 1540 | 0.5 |
| Phenoxyethanol | 0.35 |
| Methyl parahydroxybenzoate | 0.15 |
| Xanthan gum | 0.1 |

[Placebo emulsion]

| | |
|---|---|
| Purified water | 84.04 |
| 1,3-Butylene glycol | 6.0 |
| Squalane | 3.0 |
| Cetostearyl alcohol | 3.0 |
| conc. glycerin | 2.0 |
| Glyceryl monostearate | 1.2 |
| Carboxyvinyl polymer | 0.3 |
| Xanthan gum | 0.15 |
| Methyl parahydroxybenzoate | 0.15 |
| Potassium hydroxide | 0.12 |
| Propyl parahydroxybenzoate | 0.03 |
| Natural vitamin E | 0.01 |

[Placebo cream]

| | |
|---|---|
| Purified water | 67.13 |
| Squalane | 15.0 |
| 1,3-Butylene glycol | 6.0 |
| Stearic acid | 4.0 |
| Cetostearyl alcohol | 3.0 |
| Behenyl alcohol | 2.0 |
| Glyceryl monostearate | 2.0 |
| Methyl polysiloxane | 0.5 |
| Methyl parahydroxybenzoate | 0.17 |
| L-arginine | 0.1 |
| Propyl parahydroxybenzoate | 0.05 |
| Natural vitamin E | 0.05 |

Example 16

Use Test

Panels (healthy adults; N=5) were requested to use the lotion, the emulsion, and the cream prepared in Example 15, and the lotion, the emulsion, and the cream were evaluated by questionnaire. For comparison, placebo excluding the extract component was used, and the panels were asked to select the better products. The results are shown in Table 5.

Compared with placebo, all cosmetics were found to exhibit better skin penetration, moistening effect, and lack of tautoness and stickiness.

TABLE 5

| | Lotion | | Emulsion | | Cream Lavender | |
|---|---|---|---|---|---|---|
| Questionnaire items | Lavender Lace "Sylvan" | Placebo | Lavender Lace "Sylvan" | Placebo | Lace "Sylvan" | Placebo |
| Moistness (moisture-retention) | 5 | 0 | 5 | 0 | 5 | 0 |
| Nonstickiness | 5 | 0 | 5 | 0 | 5 | 0 |
| Spread | 5 | 0 | 5 | 0 | 5 | 0 |
| Penetration | 5 | 0 | 5 | 0 | 5 | 0 |
| Stickiness | 0 | 5 | 0 | 5 | 0 | 5 |

* Numbers indicate the number of people who selected the sample.

Example 17

Component Analysis of Augres "Royal Sash" Flower Extract Obtained in Example 3

Sugar content was measured by the phenol-sulfuric acid method.

[Test Method and Results]

The test was conducted in the same manner as in Example 8-(i), except that the extract was diluted 200-fold with distilled water.

Sugar content of the extract was 10,063 µg/ml, and approximately 91 wt % of the solid content (1.1 wt %) was sugars.

Example 18

Component Analysis of Marie Noel "Velano" Flower Extract Obtained in Example 5

In order to clarify the components in the extract prepared in Example 5, sugar contents were measured by the phenol-sulfuric acid method.

[Test Method and Results]

The test was conducted in the same manner as in Example 8-(i), except that the extract was diluted 200-fold with distilled water.

Sugar content of the extract was 9,238 µg/ml, and approximately 84 wt % of the solid content (1.1 wt %) was sugars.

Example 19

Sugar Composition Analysis of Augres "Royal Sash" Flower Extract Obtained in Example 3

Sugar composition analysis of the extract prepared by the method of Example 3 was carried out.

(i) Analysis Via Degradation

[Sample Preparation]

The samples were prepared in the same manner as in Example 9-(i).

[Method for Measuring Neutral Sugars]

Measurement was carried out in the same manner as in Example 9-(i).

The results of sugar composition analysis via degradation are shown in Table 6.

TABLE 6

| | Augres "Royal Sash" (μg/ml) | Marie Noel "Velano" (μg/ml) | Cymbidium (μg/ml) | Phalaenopsis (μg/ml) |
|---|---|---|---|---|
| Man | 2721.10 | 2099.25 | 155.41 | 48.21 |
| Glu | 975.13 | 1102.52 | 2368.70 | 667.82 |
| Xyl | 58.88 | 42.71 | 13.72 | 3.37 |
| Gal | 53.60 | 49.10 | 105.55 | 13.93 |
| Ara | 57.18 | 1.31 | 34.93 | 10.34 |
| Total | 3865.89 | 3294.89 | 2678.31 | 743.67 |

Man: mannose,
Glu: glucose,
Xyl: xylose,
Gal: galactose,
Ara; arabinose (ii) Analysis of Free Sugars
[Sample Preparation]
The samples were prepared in the same manner as in Example 9-(ii).
[Method for Measuring Neutral Sugars]
Measurement was carried out in the same manner as in Example 9-(ii).
The results of free sugar analysis are shown in Table 7.

TABLE 7

| | Augres "Royal Sash" (μg/ml) | Marie Noel "Velano" (μg/ml) | Cymbidium (μg/ml) | Phalaenopsis (μg/ml) |
|---|---|---|---|---|
| Fru | 1288.56 | 1730.05 | 2170.82 | 454.23 |
| Glu | 1033.90 | 1327.00 | 2137.41 | 428.81 |
| Xyl | 11.81 | 8.21 | 5.07 | 0.00 |
| Man | 14.09 | 18.56 | 0.00 | 0.83 |
| Gal | 21.30 | 18.56 | 28.31 | 1.29 |
| Total | 2369.66 | 3102.38 | 4341.61 | 885.16 |

Fru: fructose,
Glu: glucose,
Xyl: xylose,
Man: mannose,
Gal: galactose

As shown in Table 6 and Table 7, the extract obtained by the method of Example 3 was found to contain mannose, fructose and glucose, in rich. Since the content of mannose as a free sugar was low, mannose was considered to be a constitutive sugar of polysaccharides.

Example 20

Sugar Composition Analysis of Marie Noel "Velano" Flower Extract Obtained in Example 5

Sugar composition analysis of the extract prepared by the method of Example 5 was carried out.
(i) Analysis Via Degradation
[Sample Preparation]
The samples were prepared in the same manner as in Example 9-(i).
[Method for Measuring Neutral Sugars]
Measurement was carried out in the same manner as in Example 9-(i).
The results of sugar composition analysis via degradation are shown in Table 6.
(ii) Analysis of Free Sugars
[Sample Preparation]
The samples were prepared in the same manner as in Example 9-(ii).
[Method for Measuring Neutral Sugars]
Measurement was carried out in the same manner as in Example 9-(ii).
The results of free sugar analysis are shown in Table 7.

As shown in Table 6 and Table 7, the extract obtained by the method of Example 5 was found to contain mannose, fructose and glucose, in rich. Since the content of mannose as a free sugar was low, mannose was considered to be a constitutive sugar of polysaccharides.

Comparative Example 1

Sugar Composition Analysis of the Extract of a Whole *Cymbidium* Plant

Sugar composition analysis of the 50% ethanol extract of a whole *Cymbidium* plant prepared in Example 12 was carried out.
(i) Analysis Via Degradation
[Sample Preparation]
The samples were prepared in the same manner as in Example 9-(i).
[Method for Measuring Neutral Sugar]
Measurement was carried out in the same manner as in Example 9-(i).
The results of composition analysis via degradation are shown in Table 6.
(ii) Analysis of Free Sugars
[Sample Preparation]
The samples were prepared in the same manner as in Example 9-(ii).
[Method for Measuring Neutral Sugar]
Measurement was carried out in the same manner as in Example 9-(ii).
The results of free sugar analysis are shown in Table 7.

As shown in Table 6 and Table 7, the constitutive sugars of the extract were mainly glucose and fructose. Mannose content was as low as 5 wt % or lower. The composition of the sample was found to be different from that of Lavender Lace "Sylvan," Augres "Royal Sash," or Marie Noel "Velano."

Comparative Example 2

Sugar Composition Analysis of Hot Extract of *Phalaenopsis* Flower

Sugar composition analysis of the hot extract of *Phalaenopsis* flowers prepared in Example 12 was carried out.
(i) Analysis Via Degradation
[Sample Preparation]
The samples were prepared in the same manner as in Example 9-(i).
[Method for Measuring Neutral Sugar]
Measurement was carried out in the same manner as in Example 9-(i).
The results of sugar composition analysis via degradation are shown in Table 6.
(ii) Analysis of Free Sugars
[Sample Preparation]
The samples were prepared in the same manner as in Example 9-(ii).
[Method for Measuring Neutral Sugars]
Measurement was carried out in the same manner as in Example 9-(ii).
The results of free sugar analysis are shown in Table 7.

As shown in Table 6 and Table 7, the constitutive sugars of the extract were mainly glucose and fructose. Mannose content was as low as 5 wt % or lower. The composition of the sample was found to be different from that of Lavender Lace "Sylvan," Augres "Royal Sash," or Marie Noel "Velano."

Example 21

Analysis of Polysaccharide Contained in Purified Product of Augres "Royal Sash" Flower Extract Obtained in Example 3

Polysaccharides were separated and purified from the extract prepared by the method of Example 3, and sugar composition analysis was carried out.
(i) Crude Fractionation (Ethanol Precipitation)
Fractionation was carried out in the same manner as in Example 10-(i). An ethanol precipitate (3.0 g) was obtained.
(ii) Crude Fractionation (C18 Column Treatment)
Fractionation was carried out in the same manner as in Example 10-(ii). An ethanol precipitate (1.2 g) was obtained.
(iii) Separation and Purification (DEAE Column Treatment)
Purification was carried out in the same manner as in Example 10-(iii). A white purified product (44.9 mg) was obtained.
(iv) Sugar Composition Analysis
Analysis was carried out in the same manner as in Example 10-(iv).

The results of polysaccharide analysis are shown in Table 8. The purified product contained mannose and glucose. Table 9 shows the ratio of mannose to glucose in polysaccharides (by weight ratio, %). The weight ratio of mannose to glucose was about 98:2, and the product contained mannose in rich.

TABLE 8

| | Augres "Royal Sash" (DEAE column-purified product) (μg/ml) | Marie Noel "Velano" (DEAE column-purified product) (μg/ml) | Bletilla striata (Fraction obtained via ethanol precipitation) (μg/ml) |
|---|---|---|---|
| Man | 639.95 | 675.75 | 797.90 |
| Glu | 16.15 | 18.40 | 274.10 |
| Total | 656.11 | 694.15 | 1071.99 |

Man: mannose,
Glu: glucose

TABLE 9

| | Augres "Royal Sash" (DEAE column-purified product) (%) | Marie Noel "Velano" (DEAE column-purified product) (%) | Bletilla striata (Fraction obtained via ethanol precipitation) (%) |
|---|---|---|---|
| Man | 97.5 | 97.3 | 74.4 |
| Glc | 2.5 | 2.7 | 25.6 |
| Total | 100 | 100 | 100 |

Man: mannose,
Glu: glucose

Example 22

Analysis of Polysaccharide Contained in Purified Product of Marie Noel "Velano" Flower Extract Obtained in Example 5

Polysaccharides were separated and purified from the extract prepared by the method of Example 5 and sugar composition analysis was carried out.
(i) Crude Fractionation (Ethanol Precipitation)
Fractionation was carried out in the same manner as in Example 10-(i). An ethanol precipitate (2.3 g) was obtained.
(ii) Crude Fractionation (C18 Column Treatment)
Fractionation was carried out in the same manner as in Example 10-(ii). An ethanol precipitate (0.4 g) was obtained.
(iii) Separation and Purification (DEAE Column Treatment)
Purification was carried out in the same manner as in Example 10-(iii). A white purified product (54.0 mg) was obtained.
(iv) Sugar Composition Analysis
Analysis was carried out in the same manner as in Example 10-(iv).

The results of polysaccharide analysis are shown in Table 8. The purified product contained mannose and glucose. Table 9 shows the ratio of mannose to glucose (by weight ratio, %). The weight ratio of mannose to glucose was about 97:3, and the product contained mannose in rich.

Comparative Example 3

Analysis of Polysaccharide Contained in *Bletilla striata* Tubers Extract

Polysaccharides were fractionated from the extract prepared by the method of Example 5 and sugar composition analysis was carried out.
(i) Fractionation (Ethanol Precipitation)
Fractionation was carried out in the same manner as in Example 10-(i). An ethanol precipitate (4.8 g) was obtained.
(ii) Sugar Composition Analysis
Analysis was carried out in the same manner as in Example 10-(iv), except that the fraction obtained in (i) was used.

The results of polysaccharide analysis are shown in Table 8. The fraction contained mannose and glucose. Table 9 shows the ratio of mannose to glucose (by weight ratio, %). The weight ratio of mannose to glucose was about 3:1, and mannose content was lower than that in the purified products of Lavender Lace "Sylvan," Augres "Royal Sash," or Marie Noel "Velano."

Example 23

Analysis of Methylation of Purified Polysaccharide of Lavender Lace "Sylvan" Flower Extract Obtained in Example 1

To 1.85 mg of the purified product obtained via separation by the method of Example 10-(iii) from the extract obtained by the method of Example 1, 0.4 ml of dimethyl sulfoxide was added in the presence of phosphorus pentaoxide, the mixture was agitated, 40 mg of sodium hydroxide and 0.3 ml of methyl iodide were added thereto, the mixture was agitated for 4 hours for reaction. The reaction mixture was subjected to chloroform extraction to obtain methylated sugar. 90% formic acid (0.5 ml) was added to the methylated sugar in order to carry out hydrolysis at 100° C. for 2 hours, and the reaction mixture was evaporated to dryness, and further subjected to hydrolysis with 2N trifluoroacetic acid, followed by evaporation to dryness. After the product was reduced with 0.5 ml of 1% sodium borohydride, and then acetylated with the addition of 0.4 ml of acetic anhydride-pyridine to obtain partially methylated alditol acetate, which was subsequently analyzed by GC and GC/MS.
[GC Conditions]
Apparatus: GC-2000AF (Shimadzu Corporation, Japan)
Column: SPB-5 fused silica capillary 30 m×0.25 mm (I.D.) (Spelco Japan)
Carrier gas: He
Column temperature: 80° C. for 1 minute, thereafter elevating to 280° C.
Injection temperature: 280° C.
Detection mode: FID
Detector temperature: 280° C.
Amount of injection: 1 µl
Injection mode: splitless
[GC/MS Conditions]
Apparatus: Mass spectrometer JMS-700V (JEOL Ltd., Japan)
Gas chromatograph HP-6890 (Agilent Technologies)
(GC Conditions)
Column: SPB-5 fused silica capillary 30 m×0.25 mm (I.D.) (Spelco Japan)
Carrier gas: He
Column temperature: 80° C. for 1 minute, thereafter elevating to 280° C.
Injection temperature: 280° C.
Amount of injection: 1 µl
Injection mode: splitless
(MS Conditions)
Ionization method: electron impact (EI) method
Electric sector: double-focusing (inverted); acceleration voltage: 10 kV
Ionization potential: 70 eV
Ionization current: 300 µA
Temperature of ionization chamber: 250° C.
Scanning speed: 1 sec/scan (m/z 35-500)
Scanning interval: 1 sec
[Results]
The GC retention time and the mass spectra were compared with the standard mass spectra to identify the peaks, and the molar ratios were determined based on the GC peak area. The results are shown in Table 10.

TABLE 10

| Methylated sugar | molar ratio |
| --- | --- |
| 2,3,4,6-tetra-O-methyl mannose | 1.00 |
| 2,3,6-tri-O-methyl mannose | 265.33 |
| 2,6-di-O-methyl mannose | 4.95 |
| 3,6-di-O-methyl mannose | 14.03 |
| 2,3-di-O-methyl mannose | 1.82 |

The above results indicate that, among the mannose molecules that constitute polysaccharides separated from the Lavender Lace "Sylvan" flower extract, the linkage pattern that was most frequently observed was 1→4 linked mannose, and that a part of the mannose molecules were likely to be branched. The linkage patterns observed at the branched portions were 1→3, 1→4 linkage, 1→2, 1→4 linkage, and 1→6, 1→4 linkage.

Example 24

Assay for Increase of Hyaluronic Acid Production

Normal human epidermal keratinocytes (NHEK (F)) (KURABO, Japan) were seeded on a 48-well plate at 25,000 cells/cm$^2$, and the cells were cultured at 37° C. under an atmosphere of 5% $CO_2$. The medium was exchanged with the HuMedia-KG2 (KURABO, Japan) containing each test sample 5 days after the initiation of culture, the culture was conducted for additional 2 days, and hyaluronic acid in the culture supernatant was measured using a hyaluronic acid assay kit (Seikagaku Corporation, Japan). At the same time, protein content was measured using the DC Protein Assay Kit (Bio-Rad Laboratories) to determine the amount of hyaluronic acid per protein.

The Lavender Lace "Sylvan" flower extract prepared by the method of Example 1 was employed as the test sample, and the extract was added to the medium at final concentrations of 126 µg/ml, 63 µg/ml, and 31.5 µg/ml, respectively, and the final concentration of the added solvent was 0.3 vol % 1,3-butylene glycol. The solvent, 0.3 vol % 1,3-butylene glycol, was also used as a control. The results are shown in Table 11. Where the amount of hyaluronic acid produced in the control was regarded as 100%, the amount of hyaluronic acid production was determined. The Lavender Lace "Sylvan" flower extract was found to increase hyaluronic acid production significantly, compared with the control, in keratinocytes.

TABLE 11

| | Concentration (µg/ml) | Hyaluronic acid production (%) |
| --- | --- | --- |
| Control | — | 100 |
| Lavender Lace | 31.5 | 104 |
| "Sylvan" | 63 | 114 |
| | 126 | 125 |

Example 25

Assay for Increase of Ceramide Production (1)

Normal human epidermal keratinocytes (NHEK (F)) (KURABO, Japan) were seeded on a 60-mm dish at 1.5×10$^5$ cells/dish, and the cells were cultured at 37° C. under an atmosphere of 5% $CO_2$. The medium was exchanged with the HuMedia-KG2 (KURABO) containing each test sample 4 days after the initiation of culture, the culture was conducted for additional 3 days, and the cells were then harvested. A chloroform-methanol (2:1) solution (3 ml) was added to the harvested cells, which were then subjected to sonication, the solvent was removed, and the lipids were extracted. To the extracted lipids, 150 µl of 3N hydrochloric acid was added, and the mixture was heated at 100° C. for 2 hours. After the solvent was removed, 2 ml of ethyl acetate, 1.25 ml of 0.1 M acetate buffer (pH 3.7), and 250 µl of a fluorescamine solution (7 mg of fluorescamine/25 ml of acetone) were added and mixed, the upper phase separated by centrifugation was measured for fluorescence intensity (Ex: 415 nm; Em: 492 nm), and the amount of ceramide was quantified.

The Lavender Lace "Sylvan" flower extract prepared by the method of Example 1 was employed as a sample, and the extract was added to the medium at final concentrations of 126 µg/ml and 63 µg/ml, respectively, and the final concentration of the added solvent was 0.3 vol % 1,3-butylene glycol. The solvent, 0.3 vol % 1,3-butylene glycol, was also used as a control. The results are shown in Table 12. Where the amount of ceramide produced by the control was regarded as 100%, the amount of ceramide production was determined. The Lavender Lace "Sylvan" flower extract was found to increase ceramide production significantly, compared with the control, in keratinocytes.

TABLE 12

|  | Concentration (μg/ml) | Ceramide production (%) |
|---|---|---|
| Control | — | 100 |
| Lavender Lace | 63 | 113 |
| "Sylvan" (extract) | 126 | 131 |

Example 26

Assay for Increase of Ceramide Production (2)

The assay was carried out in the same manner as in Example 25, except that the ethanol precipitate of the Lavender Lace "Sylvan" flower extract obtained in Example 10-(ii) was employed as the sample. The sample was dissolved in water, and the mixture was added to the medium at a final concentration of 100 μg/ml. The control contained no substance to be assayed. The results are shown in Table 13. Where the amount of ceramide produced by the control was regarded as 100%, the amount of ceramide production was determined. The ethanol precipitate of the Lavender Lace "Sylvan" flower extract was found to increase ceramide production significantly, compared with the control, in keratinocytes.

TABLE 13

|  | Concentration (μg/ml) | Ceramide production (%) |
|---|---|---|
| Control | — | 100 |
| Lavender Lace "Sylvan" (Ethanol precipitate) | 100 | 121 |

Example 27

Assay for Increase of Ceramide Production (3)

The assay was carried out in the same manner as in Example 25, except that the purified product of the Lavender Lace "Sylvan" flower extract obtained in Example 10-(iii) was employed as the sample. The sample was dissolved in water, and each mixture was added to the medium at final concentrations of 100 μg/ml and 200 μg/ml. The control did not contain any substance to be assayed. The results are shown in Table 14. Where the amount of ceramide produced by the control was regarded as 100%, the amount of ceramide production was determined. The purified product of the Lavender Lace "Sylvan" flower extract was found to increase ceramide production significantly, compared with the control, in keratinocytes.

TABLE 14

|  | Concentration (μg/ml) | Ceramide production (%) |
|---|---|---|
| Control | — | 100 |
| Lavender Lace "Sylvan" (Purified product) | 100 | 107 |
|  | 200 | 122 |

Example 28

Examination for Increase of Type IV Collagen Production

The sample was added to the medium of the LSE-high 1-week culture/A/L culture set of a three-dimensional model of human skin (TESTSKIN™, TOYOBO, Japan), the culture was conducted at 37° C. under an atmosphere of 5% $CO_2$ for 7 days, and the culture cells were fixed with formalin to prepare parfin sections. After deparaffinization, the anti-human type IV collagen antibody (Clone PHM-12+CIV 22) (Thermo Fisher Scientific) was used as the primary antibody, and the reaction was carried out with Histofine Simple Stain MAX-PO (M) (Nichirei Biosciences Inc., Japan), followed by staining using the DAB substrate kit (Nichirei Biosciences Inc., Japan). Also, nuclear staining was carried out by hematoxylin staining Tissue was observed, and the staining intensity was compared with the control to determine the amount of type IV collagen production.

Figure 5:
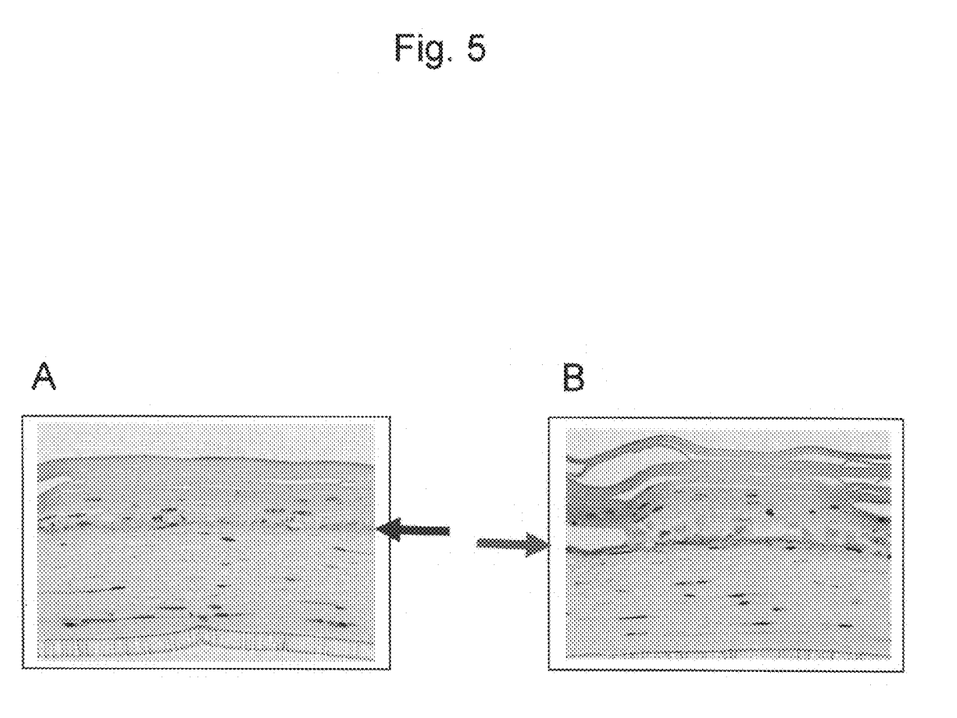
FIG. 5 shows the effect of increasing of type IV collagen production in Example 28. Panel A shows the staining results of control, and Panel B shows the staining results of the cases where the extracts of Example 1 are added.

The Lavender Lace "Sylvan" flower extract prepared by the method of Example 1 was employed as the sample, and the extract was added to the medium at a final concentration of 126 μg/ml. The control did not contain any substance to be examined. In FIG. 5, Panel A shows the staining results of the control, and Panel B shows the staining results when the extract of Example 1 was added. The arrow in the figure indicates type IV collagen. The amount of type IV collagen production was found to increase with the addition of the extract.

All publications, patents, and patent applications cited herein are incorporated herein by reference in their entirety.

The invention claimed is:

1. An extract obtained from Augres "Royal Sash" a plant of the genus *Odontoglossum* of the family Orchidaceae, or obtained from a hybrid plant of the genus *Odontoglossum* and the genus *Cochlioda*, selected from the group consisting of Lavender Lace "Sylvan" and Marie Noel "Velano," said extract having the following features (1) to (5):
   (1) the extract comprises sugar components, approximately 60% to 70% by weight of which is accounted for by polysaccharides;
   (2) 90% or more of a constitutive sugar of the polysaccharides is mannose;
   (3) mannose is linked via a β-1,4 glycosidic linkage;
   (4) the extract has a moisturizing effect; and
   (5) a part of the mannose molecules are branched at positions 2, 3 and 6.

2. The extract according to claim 1, which further has the following feature:
   (1) the extract has an effect of increasing hyaluronic acid production, an effect of increasing ceramide production, and an effect of increasing type IV collagen production.

3. The extract according to claim 1, which further has the following feature:
   (1) the extract suppresses production of lipid peroxide.

4. The extract according to claim 1, wherein the plant material for extraction contains flowers.

5. A method for preparing the extract according to claim 1, comprising the following steps of:
   mixing a plant portion containing flowers of a plant from an Augres "Royal Sash" plant of the genus *Odontoglossum* of the family Orchidaceae, or obtained from a hybrid plant of the genus *Odontoglossum* and the genus *Cochlioda*, selected from the group consisting of Lavender Lace "Sylvan" and Marie Noel "Velano, " with a solvent containing water and 1, 3-butylene glycol; heating and extracting the mixture of the plant portion and the solvent; and obtaining the extract.

6. An extract obtained from an Augres "Royal Sash" plant of the genus *Odontoglossum* of the family Orchidaceae, or obtained from a plant derived from a hybrid plant of the genus *Odontoglossum* and the genus *Cochlioda*, selected from the group consisting of Lavender Lace "Sylvan" and Marie Noel "Velano," said extract having the following features (1) to (5):
(1) the extract comprises sugar components, approximately 60% to 70% by weight of which is accounted for by polysaccharides;
(2) 90% or more of a constitutive sugar of the polysaccharide is mannose;
(3) mannose is linked via a b-1,4-glycosidic linkage;
(4) the extract has a moisturizing effect; and
(5) a part of the mannose molecules are branched at positions 2, 3 and 6 wherein the extract is obtained by the method comprising:
mixing a plant portion containing flowers of the plant with a solvent containing water and 1,3-butylene glycol;
heating the mixture of the plant portion and the solvent at a temperature of between 60° C. and 120° C. and then cooling to a temperature of between 0° C. and 60° C. for extraction; and obtaining the extract.

7. An external agent for skin comprising the extract according to claim 1 having the polysaccharide as an active ingredient.

8. The external agent for skin according to claim 7, wherein the external agent is a pharmaceutical or cosmetic.

* * * * *